United States Patent [19]

LeFiles et al.

[11] Patent Number: 5,298,253

[45] Date of Patent: Mar. 29, 1994

[54] COPPER HYDROXIDE DRY FLOWABLE BACTERICIDE/FUNGICIDE AND METHOD OF MAKING AND USING SAME

[75] Inventors: James H. LeFiles, Valdosta; Evelyn J. Taylor, Hahira; Mark A. Crawford, Valdosta, all of Ga.

[73] Assignee: Griffin Corporation, Valdosta, Ga.

[21] Appl. No.: 928,148

[22] Filed: Aug. 11, 1992

Related U.S. Application Data

[63] Continuation of Ser. No. 591,288, Oct. 1, 1990, abandoned.

[51] Int. Cl.$^5$ .................. A01N 59/20; A61K 31/78
[52] U.S. Cl. ................................ 424/409; 424/630; 424/633; 424/78.33
[58] Field of Search .............. 424/78, 80, 78.08, 78.1, 424/630, 633, 409; 514/772.6

[56] References Cited

U.S. PATENT DOCUMENTS

| Re. 24,324 | 5/1957 | Furness | 423/604 |
|---|---|---|---|
| 3,428,731 | 2/1969 | Furness | 424/633 |
| 3,954,967 | 5/1976 | Urton | 514/531 |
| 4,003,994 | 1/1977 | Downer et al. | 424/630 |
| 4,048,324 | 9/1977 | Kohn | 514/500 |
| 4,244,836 | 1/1981 | Frensch et al. | 264/4.6 |
| 4,339,448 | 7/1982 | Dockner et al. | 424/245 |
| 4,409,358 | 10/1983 | Kraft et al. | 524/547 |
| 4,418,056 | 11/1983 | Gonzalez | 424/631 |
| 4,528,185 | 7/1985 | Kraft et al. | 424/78.26 |
| 4,732,762 | 3/1988 | Sjogren | 514/722 |
| 4,770,694 | 9/1988 | Iwasaki et al. | 514/483 |
| 4,770,694 | 9/1988 | Iwasaki et al. | 514/483 |
| 4,923,866 | 5/1990 | Albert et al. | 514/483 |

FOREIGN PATENT DOCUMENTS

| 914962 | 7/1946 | France . |
| 916489 | 8/1946 | France . |
| 943010 | 9/1948 | France . |
| 966315 | 3/1950 | France . |
| 493148 | 3/1938 | United Kingdom . |
| 880270 | 10/1961 | United Kingdom . |
| 994830 | 6/1965 | United Kingdom . |

OTHER PUBLICATIONS

Goodrite K-700, Aug. 1987, B. F. Goodrich.
Koride 101, Griffin Corp.
N. Yamamori et al., "Application of Polymers Containing Copper Salts to Antifouling Paint".
A. Kondo, "Microcapsule Processing and Technology," 1979.
Copies of two CASSIS searches.
M. Mandel, "Charge Interactions and Association in Polyelectrolyte Solutions. I. Some General Remarks".
V. Crescenzi et al., "Thermodynamics of Polycarboxylate Aqueous Solutions. I. Dilatometry and Calorimetry of Protonation and Coopper (11) Binding".

(List continued on next page.)

Primary Examiner—Thurman K. Page
Assistant Examiner—Peter F. Kulkosky
Attorney, Agent, or Firm—Jones & Askew

[57] ABSTRACT

There is disclosed a granular copper hydroxide dry flowable bactericide/fungicide having improved biological activity and a method for making and using same. A bactericide/fungicide is made by forming a homogeneous aqueous slurry containing between approximately 5% and 20% by weight (based on the total weight of all dry ingredients) of a first dispersant selected from the group consisting of partially neutralized polyacrylic acid having a pH of between approximately 5 and 10 and an average molecular weight of between approximately 1,000 and 10,000 and lignin sulfonate, between approximately 0% and 5% by weight (based on the total weight of all dry ingredients) of a second dispersant for bentonite clay, between approximately 40% and 80% by weight (based on the total weight of all dry ingredients) phosphate stabilized cupric hydroxide and between approximately 6% and 30% by weight (based on the total weight of all dry ingredients) bentonite clay; and spray drying the slurry to thereby form a dry free flowing granular bactericide/fungicide product. The slurry can also include antifoam and wetting agents. Other partially neutralized polycarboxylic acid polymers useful as the first dispersant are also disclosed.

30 Claims, No Drawings

OTHER PUBLICATIONS

M. Morcellet, "Microcalorimetric Investigation of the Association of Syndiotactic Poly(Methacrylic Acid) with some Divalent Metal Ions".

C. Travers, et al. "The Complexing of Ca(II), Co(II), and Zn(II) by Polymetharcylic and Polyacrylic Acid".

R. Subramanian, "X-ray Studies on Interpolymer Adducts Formed between Poly(N-vinylpyrrolidone and Poly(acrylic acid)s".

H. Yokoi, "Interaction Modes between Heavy Metal Ions and Water-Soluble Polymers. 1. Spectroscopic and Magnetic Reexamination of the Aqueous Solutions of Cupric Ions and Poly(vinyl alcohol)".

M. Mandel, "Interaction of Polymethacrylic Acid and Bivalent Counterions".

M. Mandel, "Interaction of Poly(methacrylic Acid) and Bivalent Counterions".

S. Paoletti, et al. "Thermodynamics of Polycarboxylate Aqueous Solutions 3. Binding of Divalent Ions".

F. Yamashita, "Study of Metal-Polycarboxylate Complexes Employing Ion-Selective Electrodes" Cu(II) and Cd(II) Compexes with Poly(acrylic acid) and Poly(itaconic acid).

S. Paloletti, "A Spectroscopic Investigation of Complexes of Divalent Metal Ions with Maleic Acid Copolymers".

W. Anspach, "Complexing of Nickel(II) and Cobalt(II) by a Polymethacrylic Acid Gel and Its Linear Polyelectrolyte Analog".

S. Noji, "Electron Spin Resonance Study of Poly(a-L-glutamic acid) and Poly(acrylic acid) Copper(II) Complexes in the Frozen State with Emphais on the Complex Species".

S. Inoue, "Polarographic Investigation of Biopolymers. III. Comparison between Poly(acrylic acid) and Poly(a, L-glutamic acid) as Regards the Complexing Behavoir toward the Copper(II) Cadmium(II), and Nickel(II) Ions in the pH Range 3-7".

S. Fang, "Ionic Conductivity of Polyacid-Poly(Vinyl Alcohol)-Metal Ion Complex Membranes".

S. Das, "Photochemistry of Copper(II)-Poly(acrylic acid)Complexes: Photogeneration and Photolysis of an Alkyl-Copper Intermediate".

S. Krupin, "Metal-Polymer Complexes Based on Hydrolyzed Polyacrylonitrile".

P. McCluskey, "Infrared Spectral Studies of Various Metal Polyacrylates".

H. Nishide, "Complexation of Poly(acrylic acid)s with Uranyl Ion".

G. Manzini, "Copper(II) Binding by Natural Ionic Polysaccharides. Part I. Potentiometric and Spectroscopic Data".

S. Chatterjee, "Study of multicomponent complexes between polycarboxylic acid, transition metal ions and non-ionic polymers".

H. Gregor, "Metal-Polyelectrolyte Complexes. II. Complexes of Copper with Cross-Lined Polyacrylic and Polymethacrylic Acids".

E. Loebl, "Metal-Polelectrolyte".

Chem. Ab.94:11630.

Chem. Ab. 91:75843q.

COPPER HYDROXIDE DRY FLOWABLE BACTERICIDE/FUNGICIDE AND METHOD OF MAKING AND USING SAME

This is a continuation of U.S. application Ser. No. 07/591,288, filed Oct. 1, 1990, now abandoned.

FIELD OF INVENTION

The present invention relates to an improved agricultural bactericide/fungicide and to a method for producing a dry flowable formulation of cupric hydroxide. More particularly, the present invention relates to a dry flowable cupric hydroxide agricultural bactericide/fungicide formulation having improved biological activity and to the method of making and using the same.

BACKGROUND OF THE INVENTION

Bactericides/fungicides are known in the art as agents used to protect agricultural crops from damage caused by pathogenic bacteria/fungi. The use of such products is necessitated by the great losses caused by such organisms. To be economical, the cost of controlling plant diseases by the application of a bactericide/fungicide product must be offset by increased crop yield and quality.

Agricultural bactericides/fungicides are available in different types of formulations including wettable powders, emulsifiable concentrates, water-based flowables, and dry flowables (also known as water dispersible granules). Dry flowable products are generally dustless, free-flowing, granular products. Dry flowable formulations have recently gained in popularity among users because they offer advantages such as improved shelf life, substantially no dusting, easy pouring, a higher percentage of active ingredient, and more convenient packaging than other formulation types.

Copper based bactericides/fungicides are used extensively in agriculture. Several dry flowable copper based bactericides/fungicides are known in the art, these being: "Kocide DF" available from Griffin Corporation of Valdosta, Ga.; "Blueshield DF" and "Nu-Cop WDG" available from Micro Flo Company of Lakeland, Fla.; and "Sandoz COC DF" and "Sandoz $Cu_2O$ DF" available from Sandoz Ltd. of Switzerland.

Cupric hydroxide by itself is unstable. However, it is known in the art that cupric hydroxide can be stabilized by a phosphate process. U.S. Pat. No. Re. 24,324 (the disclosure of which is incorporated herein by reference) relates to a method of making stable cupric hydroxide. U.S. Pat. No. 3,428,731 (the disclosure of which is also incorporated herein by reference) relates to dispersions of phosphate stabilized cupric hydroxide. That patent discloses that aqueous dispersions of finely divided phosphate-process cupric hydroxide can be prepared by carefully regulating the pH of the dispersion and the calcium hardness of the aqueous vehicle. The patent also discloses that approximately 1% to 3% by weight of a didpersant should be added to the aqueous vehicle before the phosphate-process cupric hydroxide is added. Suitable dispersing agents are disclosed as including sodium lignosulfonate, the sodium salt of a polymeric carboxylic acid, sulfonated naphthalene, technical protein colloid, tallow dimethyl benzyl ammonium chloride, the sodium salt of polymerized alkyl aryl sulfonic acid, diethanolamide of a special fraction of coconut fatty acids, the sodium salt of condensed mono-naphthalene sulfonic acid and isooctyl phenyl polyethoxy ethanol.

The prior art copper based bactericide/fungicide products require the use of relatively large amounts of copper to effectively control disease. This relatively high level of copper detracts from cost effectiveness, contributes to soil residue problems and raises the potential for phytotoxicity. In addition, the methods used to produce these prior art products are not always cost effective.

Therefore, a need exists for a dry flowable copper based bactericide/fungicide formulation and a cost effective method for producing a dry flowable copper based bactericide/fungicide formulation which provides increased biological activity compared to conventional dry products and with a lower copper use rate when applied to crops.

SUMMARY OF THE INVENTION

The present invention satisfies the above-described needs by providing an improved copper based dry flowable bactericide/fungicide formulation and a cost effective method of producing and using such a formulation which provides improved biological activity when applied to crops for bactericide/fungicide purposes and requires the application of less copper for effective bactericide/fungicide protection than previously known dry formulations of copper based bactericide/fungicide products.

Generally, the method of making the formulation of the present invention comprises the steps of forming an aqueous slurry by combining with water between approximately 5% and 20% by weight (based on the total weight of all dry ingredients) of a first dispersant selected from the group consisting of partially neutralized polyacrylic acid having a pH of between approximately 5 and 10 and having an average molecular weight of between approximately 1,000 and 10,000 and lignin sulfonate; between approximately 0% and 5% by weight (based on the total weight of all dry ingredients) of a dispersant for bentonite clay; between approximately 40% and 80% by weight (based on the total weight of all dry ingredients) phosphate stabilized cupric hydroxide; and between approximately 6% and 30% by weight (based on the total weight of all dry ingredients) bentonite clay; mixing those ingredients to form a substantially homogeneous slurry; and spray drying the slurry to produce a granular material having less than 10% moisture.

The improved formulation of the present invention comprises a granule having less than 10% moisture and consisting essentially of between approximately 40% and 80% by weight (based on the total weight of all dry ingredients) phosphate stabilized cupric hydroxide; between approximately 5% and 20% by weight (based on the total weight of all dry ingredients) of a first dispersant selected from the group consisting of partially neutralized polyacrylic acid having a pH of between approximately 5 and 10 and having an average molecular weight of between approximately 1,000 and 10,000 and lignin sulfonate; between approximately 0% and 5% by weight (based on the total weight of all dry ingredients) of a dispersant for bentonite clay; and between approximately 6% and 30% by weight (based on the total weight of all dry ingredients) bentonite clay.

The method of the present invention for controlling bacterial/fungal diseases in plants comprises the step of applying to said plants an aqueous dispersion formed from a composition consisting essentially of between approximately 40% and 80% by weight (based on the total weight of all dry ingredients) phosphate stabilized cupric hydroxide; between approximately 5% and 20% by weight (based on the total weight of all dry ingredients) of a first dispersant selected from the group consisting of partially neutralized polyacrylic acid having a pH of between approximately 5 and 10 and having an average molecular weight of between approximately 1,000 and 10,000 and lignin sulfonate; between approximately 0% and 5% by weight (based on the total weight of all dry ingredients) of a second dispersant for bentonite clay; and between approximately 6% and 30% by weight (based on the total weight of all dry ingredients) bentonite clay.

Accordingly, it is an object of the present invention to provide an improved dry flowable copper based bactericide/fungicide formulation and to provide an improved method of making and using the same.

A further object of the present invention is to provide a copper based bactericide/fungicide having improved biological activity when applied to crops for bactericide/fungicide purposes and which requires the application of less copper for effective bactericide/fungicide protection than previously known dry formulations of copper based bactericide/fungicide products.

Another object of the present invention is to provide a copper based bactericide/fungicide formulation which when applied to crops provides reduced soil residue and potential for phytotoxicity.

Yet another object of the present invention is to provide a cost effective method for producing a copper bactericide/fungicide having improved biological activity.

Still another object of the present invention is to provide a bactericide/fungicide which has improved rainfastness when applied to plants.

These and other objects, features and advantages of the present invention will become apparent after a review of the following detailed description of the preferred embodiment.

DETAILED DESCRIPTION OF A PREFERRED EMBODIMENT

The invention relates to an improved agricultural bactericide/fungicide formulation and to a cost effective method for producing a dry flowable formulation of cupric hydroxide. The novel product of the present invention offers improved biological activity over typical cupric hydroxide dry products, while requiring significantly less copper in its formulation. The decreased copper content reduces the bactericide/fungicide formulation's contribution to soil accumulation of copper and reduces the potential for phytotoxicity.

A bactericide/fungicide formulation may be produced in accordance with the present invention by the following steps. Between approximately 5% and 20% by weight (based on the total weight of all dry ingredients) of a first dispersant selected from the group consisting of partially neutralized polyacrylic acid having a pH of between approximately 5 and 10 and having an average molecular weight of between approximately 1,000 and 10,000 and lignin sulfonate is combined with water followed by the addition of between approximately 0% and 5% by weight, preferably between approximately 1% to 5% by weight (based on the total weight of all dry ingredients) of a dispersant for bentonite clay. Preferably the first dispersant is added to the water before the dispersant for the bentonite clay. Between approximately 40% and 80% by weight, preferably between approximately 60% and 80% by weight (based on the total weight of all dry ingredients) of phosphate stabilized cupric hydroxide and between approximately 6% and 30% by weight (based on the total weight of all dry ingredients) bentonite clay are then added to the aqueous mixture to form a slurry. The amount of water to which the foregoing ingredients are added is not critical to the present invention. However to avoid excessive drying requirements, it is preferred that the final slurry composition contains between approximately 55% and 80% by weight (based on the total weight of the slurry) water, preferably between 65% and 70%. The foregoing ingredients are then mixed together, using conventional mixing equipment and conventional mixing techniques well known in the art, for a period of time sufficient to produce a substantially homogeneous slurry. The slurry is then spray dried in conventional spray drying equipment, also well known in the art, to produce a granular material having less than 10% moisture, preferably less than 5% moisture and, most preferably less than 3% moisture.

The partially neutralized polyacrylic acid useful in the present invention is prepared by partially neutralizing polyacrylic acid having a molecular weight of between approximately 1,000 and 10,000, preferably between approximately 2,000 and 5,000, and most preferably having a molecular weight of approximately 2,000. The polyacrylic acid is partially neutralized to a pH of between approximately 5 and 10, preferably between approximately 6 and 8, by adding to the polyacrylic acid a neutralizing agent. The neutralizing agent is not critical to the present invention, however, suitable neutralizing agents include sodium hydroxide; potassium hydroxide; $NaHCO_3$; $Na_2CO_3$; $NH_4OH$, $R_4N^+OH^-$ wherein R is either $CH_3$ or $C_2H_5$; primary amines, such as methyl, ethyl, n-propyl, isopropyl, t-butyl; secondary amines, such as dimethyl, diethyl, di-n-propyl and di-isopropyl; and tertiary amines, such as trimethyl, triethyl, and tri-n-propyl.

The resulting partially neutralized polyacrylic acid is therefore a combination of a copolymer of acrylic acid and a polyacrylic salt thereof, such as sodium polyacrylate. Suitable partially neutralized polyacrylic acids are commercially available. Such commercially available products include "Good-rite K-752" available from B. F. Goodrich Co. of Cleveland, Ohio. "Good-rite K-752" is a polyacrylic acid, partial sodium salt in water having the formula $(C_3H_4O_2)_x(C_3H_3NaO_2)_y$; and DP6-2696 and DISPEX N40 both salts of polymeric carboxylic acid in aqueous solution available from Allied Colloids, Inc. of Suffolk, Va.

Other partially neutralized polycarboxylic acids can also be used as the first dispersant of the present invention. Suitable polycarboxylic acids useful in the present invention include polymethacrylic acids; copolymers of acrylic acid and acrylamide, methacrylamide, acrylate esters (methyl, ethyl and butyl), methacrylic acid, methacrylate esters (methyl and ethyl) and maleic anhydride; carboxymethylcellulose; and maleic acid polymers and copolymers with butadiene and maleic anhydride. The neutralizing agents, pH of the partially neutralized acids and the molecular weight ranges of these additional carboxylic acids are the same as for the polyacrylic acids as set forth above.

Lignin sulfonate is well known in the art and many are commercially available. The particular type of lignin sulfonate useful in the present invention is not critical. For example, a lignin sulfonate useful in the present invention is available under the trademark REAX 88B, a sodium salt of chemically modified, low molecular weight, kraft lignin polymer solubilized by four sulfonate groups, available from Westvaco Chemical Division, Charleston Heights, S.C.

Dispersants for bentonite clay are well known in the art. The particular dispersant for bentonite clay is not critical to the present invention. The dispersant for bentonite clay is used to sufficiently reduce the viscosity of the slurry to permit spray drying of the slurry. Therefore, any dispersant system which permits spray drying of the slurry is useful in the present invention. A preferred dispersant useful in the present invention is sodium tripolyphosphate. Other dispersants for bentonite clay useful in the present invention include tetrasodium pyrophosphate and sodium lignin sulfonates. The foregoing dispersants may be used alone or in combination with the sodium tripolyphosphate.

Phosphate stabilized cupric hydroxide is also well known in the art and is commercially available. Such commercially available products include KOCIDE® cupric hydroxide, a phosphate stabilized cupric hydroxide formulation grade agricultural fungicide containing 88% copper hydroxide and 12% inerts available from Griffin Corporation of Valdosta, Ga. Methods of producing phosphate stabilized cupric hydroxide are also disclosed in U.S. Pat. Nos. 3,428,731 and Re. 24,324. The phosphate stabilized copper hydroxide of the present invention is preferably added to the slurry in the form of a wet cake comprising approximately 35% by weight technical phosphate stabilized cupric hydroxide in water.

Bentonite clay is well known in the art. A bentonite clay useful in the present invention is highly purified, i.e., wet milled, sieved and fractioned to collect particles less than approximately 2µ. Such a highly purified bentonite clay is commercially available under the trademark "Veegum F," a hydrated magnesium aluminum silicate mineral or smectite clay available from R. T. Vanderbilt Company, Inc. of Norwalk, Conn. The preferred bentonite clay is available under the trademark "Volclay HPM-75," a high purity air-floated sodium bentonite clay consisting of micron-sized particles (dry particles having a minimum of 99% finer than 200 mesh and 98% finer than 325 mesh) available from American Colloid Company of Arlington Heights, Ill.

The slurry can also optionally include compounds such as antifoam agents and wetting agents to aid in the formulation of a homogeneous slurry. Antifoam agents and wetting agents for aiding in the preparation of slurries are well known in the art. Wetting agents useful in the present invention include "Tamol 731 SD," an anionic, polymer-type dispersant available from Rohm & Haas Co. of Philadelphia, Pa. Antifoam agents useful in the present invention include "Surfynol 104E," a surfactant having the formula $C_{14}H_{26}O_2$ dissolved in ethylene glycol, available from Air Products and Chemicals, Inc. of Allentown, Pa. and "ANTIFOAM FG-10," a dimethylsilicone emulsion, available from Dow Chemical Company of Midland, Mich. Wetting agents and antifoam agents can each be incorporated into the slurry in the amounts of between approximately 0.03% and 1.0% by weight (based on the total weight of all dry ingredients).

The slurry is optionally milled using conventional milling equipment and milling techniques well known in the art to reduce the average particle size of the particles in the slurry. The milling process should be conducted so as to reduce the particles in the slurry to an average particle size of between approximately 0.5 and 3.0 microns, preferably between approximately 2.0 and 2.4 microns, as measured on a conventional Coulter counter.

The slurry is then dried in conventional drying equipment, preferably by spray drying using a spray dryer equipped with either a single fluid nozzle or a rotating disk and having an inlet temperature between approximately 350° and 480° F. and an outlet temperature between approximately 150° and 260° F. to form a dry free flowing granular product therefrom. Spray drying equipment and techniques for spray drying dispersions are well known in the art.

The components of the present invention are believed to act in the following manner to produce a bactericide/fungicide requiring less active ingredient, i.e., cupric hydroxide, yet providing enhanced biological activity. Upon dilution into water, it is believed that the clay swells and mechanically aids breakdown of the agglomerate to the primary cupric hydroxide particles. The first dispersant (polyacrylate/lignin sulfonate) is believed to coat the primary particles to form a stable dispersion of the particles to thereby enhance distribution of the particles on the leaf surface upon sprayout. The second dispersant (sodium tripolyphosphate) is believed to aid in the formation of a stable dispersion upon dilution, but primarily lowers the viscosity of the slurry to allow spray-drying at a high solids content, thereby reducing drying costs. Furthermore, after drying on a leaf surface, the formulation is more resistant to erosion by rain, dew, or wind than conventional dry formulations.

The bactericide/fungicide of the present invention may be applied directly to the leaves of a plant to control bacterial/fungus diseases. The bactericide/fungicide is applied by mixing with water and spraying the resulting dispersion onto the plants using conventional agricultural sprayers and spraying techniques well known in the art. The bactericide/fungicide granules of the present invention are preferably mixed with water and applied to the leaves of plants by spraying (either aerial or ground) or by chemigation at a rate of between approximately 0.5 and 16 pounds per acre in a volume of water of between approximately 3 and 800 gallons per acre.

The bactericide/fungicide of the present invention is useful for treating bacterial and fungal diseases on various plants including citrus, such as grapefruit, lemon, lime, orange, tangelo and tangerine; field crops, such as alfalfa, oats, peanuts, potatoes, sugar beets, wheat, and barley; small fruits, such as blackberry, cranberry, currant, gooseberry, raspberry and strawberry; tree crops, such as almond, apple, apricot, avocado, banana, cacao, cherry, coffee, filberts, mango, nectarine, olive, peach, pear, pecan, plum, prune and walnut; vegetables, such as beans, broccoli, brussel sprout, cabbage, cantaloupe, carrot, cauliflower, celery, collards, cucumber, eggplant, honeydew, muskmelon, onions, peas, peppers, pumpkin, squash, tomato and watermelon; vines, such as grape, hops and kiwi; miscellaneous, such as ginseng, live oak and sycamore and ornamentals, such as aralia, azalea, begonia, bulbs (Easter lily, tulip, gladiolus), carnation, chrysanthemum, cotoneaster, euonymus, India hawthorn, ivy, pachysandra, periwinkle, philodendron, pyracantha, rose and yucca (Adams-Needle).

The bactericide/fungicide of the present invention is useful for treating plants with bacterial or fungal diseases, such as melanose, scab, pink pitting, greasy spot, brown rot, phytophthora, citrus canker, xanthomonas and cerospora leaf spots, black leaf spot (alternaria), alternaria blight, botrytis blight, powdery mildew, xanthomonas leaf spot, anthracnose, pseudomonas leaf spot, septoria leaf spot, entomosporium leaf spot, volutella leaf blight, phomopsis stem blight, bacterial leaf spot, fire blight, black spot, leaf curl, coryneum blight (shot hole), blossom blight, pseudomonas blight, shuck and kernal rot (*Phytophthora cactorum*), zonate leafspot (*Cristulariella pyramidalis*), walnut blight, bacterial blight (halo and common), brown spot, black rot (xanthomonas), downy mildew, cercospora early blight, septoria late blight, angular leaf spot, phomopsis, purple blotch, bacterial speck, gray leaf mold, septoria leaf spot, dead bud (*Pseudomonas syringae*), *Erwinia herbicola, Pseudomonas fluorescens*, stem blight, ball moss, leptosphaerulina leaf spots, helminthosporium spot blotch, leaf spot, cane spot, fruit rot, blossom brown rot, bacterial blast (pseudomonas), European canker, crown or collor rot, sigatoka, black pitting, black pod, coffee berry disease (*Collectotrichum coffeanum*), leaf rust (*Hemileia vastatrix*), iron spot (*Cercospora coffeicola*), pink disease (*Corticium salmonicolor*) eastern filbert blight, and peacock spot.

The following examples are illustrative of the present invention and are not intended to limit the scope of the invention as set forth in the appended claims.

EXAMPLE 1

The following ingredients are combined and mixed together to form a substantially homogeneous slurry:

|  | lbs |
| --- | --- |
| Water | 490 |
| Dispex N40 | 44 |
| Reax 88B | 53 |
| Sodium Tripolyphosphate | 30 |
| Cu(OH)$_2$ wetcake (35.4% Cu(OH)$_2$ technical) | 2155 |
| Volclay HPM-75 | 167 |
|  | 2939 |

The resulting slurry is then milled to produce an average particle size of approximately 2.0 microns. The slurry is then spray dried in a conventional spray dryer equipped with a single fluid nozzle and having an inlet temperature of 375° F. and an outlet temperature of 190° F. The resulting granular product is dry (water content less than 3%), is free flowing and has an average granule size of approximately 130 microns.

EXAMPLE 2

A slurry is made as in Example 1 using the following ingredients:

|  | lbs |
| --- | --- |
| Water | 1867 |
| Good-rite K-752 | 114 |
| 50% NaOH in water | 56 |
| Sodium Tripolyphosphate | 30 |
| Tamol 731 SD | 2 |
| Cu(OH)$_2$ technical | 708 |
| Volclay HPM-75 | 160 |
| Surfynol 104E | 2 |
|  | 2939 |

The slurry is spray dried as in Example 1 except that the air inlet temperature is 390° F. and the air outlet temperature is 210° F. The resulting granular product is dry (water content less than 5%), is free flowing and has an average granule size of approximately 100 microns.

EXAMPLE 3

A slurry is made as in Example 1 using Allied DP62696 as the sodium polyacrylate as follows:

|  | lbs |
| --- | --- |
| Water | 645 |
| Allied DP6-2696 | 220 |
| Sodium Tripolyphosphate | 30 |
| Tamol 731 SD | 2 |
| Cu(OH)$_2$ wetcake (35.4% Cu(OH)$_2$ technical) | 2000 |
| Volclay HPM-75 | 160 |
| Surfynol 104E | 2 |
|  | 2939 |

The slurry is milled to an average particle size of approximately 2.4 microns. The slurry is then spray dried as in Example 1 except that the air inlet temperature is approximately 460° F. and the outlet temperature is 240° F. The resulting product is a dry, free flowing granular product having a moisture content of less than 3% and an average granular size of approximately 150 microns.

EXAMPLE 4

A slurry having the following formula is made as in Example 1:

|  | lbs |
| --- | --- |
| Water | 570 |
| Good-rite K-752 | 114 |
| 50% NaOH in water | 56 |
| Sodium Tripolyphosphate | 30 |
| Tamol 731 SD | 2 |
| Cu(OH)$_2$ wetcake (35.4% Cu(OH)$_2$ technical) | 2000 |
| Volclay HPM-75 | 161 |
| Antifoam FG-10 | 6 |
|  | 2939 |

The slurry is spray dried in a conventional spray dryer equipped with a rotary disk atomizer and having an inlet temperature of 420° F. and an outlet temperature of 170° F. The resulting granular product has an average granule size of approximately 150 microns, a water content of less than 3% and is free flowing.

EXAMPLE 5

A slurry is made as in Example 3, except that the slurry is made from the following ingredients:

|  | lbs |
| --- | --- |
| Water | 575 |
| Good-rite K-752 | 114 |
| 50% NaOH in water | 56 |
| Sodium Tripolyphosphate | 30 |
| Tamol 731 SD | 2 |
| Cu(OH)$_2$ wetcake (35.4% Cu(OH)$_2$ technical) | 2000 |
| Volclay HPM-75 | 160 |
| Surfynol 104E | 2 |
|  | 2939 |

The slurry is spray dried as in Example 3 and produces a dry, free flowing granular product.

|  | lbs |
|---|---|
| Water | 553 |
| Dispex N40 | 327 |
| Sodium Tripolyphosphate | 28 |
| Cu(OH)2 wetcake (35.4% Cu(OH)2 technical) | 2000 |
| Volclay HPM-75 | 123 |
|  | 3031 |

The slurry is spray dried at an air inlet temperature of 410° F. and an outlet temperature of 220° F. and produces a dry, free flowing granular product.

EXAMPLE 7

A slurry having the following formula is made as in Example 1:

|  | lbs |
|---|---|
| Water | 739 |
| Dispex N40 | 354 |
| Sodium Tripolyphosphate | 30 |
| Cu(OH)2 wetcake (35.4% Cu(OH)2 technical) | 2000 |
| Veegum F | 110 |
|  | 3233 |

The slurry is spray dried as in Example 2 and produces a dry, free flowing granular product.

EXAMPLE 8

A slurry having the following formula is made as in Example 1:

|  | lbs |
|---|---|
| Water | 551 |
| Good-rite K-759 | 120 |
| Sodium Tripolyphosphate | 30 |
| Tamol 731 SD | 2 |
| Cu(OH)2 wetcake (35.4% Cu(OH)2 technical) | 2000 |
| Volclay HPM-75 | 143 |
| Antifoam FG-10 | 6 |
|  | 2852 |

The slurry is spray dried as in Example 2 and produces a dry, free flowing granular product.

EXAMPLE 9

A slurry having the following formula is made as in Example 1:

|  | lbs |
|---|---|
| Water | 645 |
| Good-rite K-759 | 100 |
| Sodium Tripolyphosphate | 50 |
| Cu(OH)2 wetcake (35.4% Cu(OH)2 technical) | 2000 |
| Volclay HPM-75 | 144 |
|  | 2939 |

The slurry is spray dried as in Example 2 and produces a dry, free flowing granular product.

EXAMPLE 10

A slurry having the following formula is made as in Example 1:

|  | lbs |
|---|---|
| Water | 484 |
| Reax 88B | 60 |
| Sodium Tripolyphosphate | 35 |
| Cu(OH)2 wetcake (33.5% Cu(OH)2 technical) | 2155 |
| Volclay HPM-75 | 165 |
|  | 2899 |

The slurry is spray dried as in Example 2 and produces a dry, free flowing, granular product.

EXAMPLE 11

A greenhouse bioassay test that is sensitive enough to detect formulation changes is used. This test utilizes *Colletotrichum lagenarium*—the cause of anthracnose on cucumbers. A dry flowable cupric hydroxide bactericide/fungicide, prepared according to Example 5, is compared at equal rates of product (0.02, 0.08, and 0.32 g/100 ml water) to commercial wettable powder formulations of copper hydroxide (Kocide ® 101 and Blue Shield TM). Treatments are replicated 5 times with 2 plants per pot. Cucumber plants are sprayed and allowed to dry at which time they are inoculated with spores of *C. lagenarium*. Inoculated plants are incubated at 100% relative humidity for 48 hours. When disease symptoms appear, individual lesions are counted on leaves and the number of lesions is used to determine chemical efficacy.

The bactericide/fungicide prepared according to Example 5 is also compared at equal rates of product (0.02, 0.08, and 0.32 g/100 ml water) to a dry flowable formulation of copper oxychloride (Nu-Cop COC) for the control of cucumber anthracnose caused by *Colletotrichum lagenarium* by the above-described method. Table 1 below shows the number of lesions on cucumber plants inoculated with *Colletotrichum lagenarium* when treated with copper fungicides.

TABLE 1

| Copper Fungicide | % Cu | g. product/100 ml water | | | Average | % Disease Control |
|---|---|---|---|---|---|---|
| | | 0.02 | 0.08 | 0.32 | | |
| | | No. lesions/leaf | | | | |
| Example 5 | 40 | 100 | 75 | 53 | 76 | 70 |
| Kocide 101 | 50 | 120 | 81 | 66 | 89 | 64 |
| Blue Shield | 50 | 147 | 112 | 78 | 112 | 55 |
| Nu-Cop COC | 50 | 211 | 159 | 145 | 172 | 31 |
| Untreated Control | — | — | — | — | 251 | 0 |

As shown in Table 1, disease control provided by the formulation made in accordance with Example 5 is better than the other formulations of copper hydroxide which contain 20% more metallic copper. Disease control provided by the formulation of Example 5 is also better than the dry flowable copper oxychloride which contains 20% more metallic copper. See Table 1.

EXAMPLE 12

A bactericide/fungicide prepared according to Example 6 is compared to Kocide 101 on tomatoes for the control of bacterial speck caused by *Pseudomonas syringae*. The two formulations are applied at equal rates (2 lbs/acre). When evaluations are made for disease incidence, untreated plants have 41% disease, Kocide 101 treated plants have 20% disease and plants treated with the bactericide/fungicide of Example 4 have 19% disease. Since the bactericide/fungicide of Example 4 contains 20% less copper than Kocide 101, this represents a significant increase in activity for the bactericide/fungicide of the present invention.

EXAMPLE 13

A bactericide/fungicide prepared according to Example 7 is compared to Kocide 101 on apricots for the control of shot hole and brown rot caused by *Coryneum beijerinckii* and *Monilinia fructicola*, respectively. They are applied at equal rates (12 lbs/acre). When evaluations are made for disease incidence, the average number of shot hole lesions per leaf are 24.5 in untreated plants, 9.5 in Kocide 101 treated plants and 6.0 in plants treated with the bactericide/fungicide of Example 6. The number of brown rot strikes per 100 shoots is 55 in the untreated plants, 33 in Kocide 101 treated plants and 26 in the plants treated with the bactericide/fungicide of Example 6. The bactericide/fungicide of Example 6 contains 20% less copper than Kocide 101, and, thus, represents a significant increase in activity in the bactericide/fungicide of the present invention.

EXAMPLE 14

The bactericide/fungicide prepared according to Example 4 is compared to Kocide 101 on lemons for the control of brown rot caused by *Phytophthora citrophthora*... The two formulations are applied at equal rates (4 lbs/acre). When evaluations are made 60 days after treatment, Kocide 101 treated fruit show 79% disease control and fruit treated with the bactericide/fungicide of Example 4 show 81% disease control. Since the bactericide/fungicide of Example 4 contains 20% less copper than Kocide 101, these results demonstrate a significant increase in activity for the bactericide/fungicide of the present invention.

EXAMPLE 15

One of the characteristics of a good fungicide is its ability to remain on a leaf surface after a rainfall. This characteristic is referred to as rainfastness.

Rainfastness of a bactericide/fungicide prepared according to Example 5 is compared to other wettable powder formulations of copper hydroxide. Pinto bean and bell pepper plants are sprayed with each product and allowed to dry. Leaves are sampled for the amount of copper deposited. After 24 hours, plants are subjected to 0.5 and 2.0 inches of simulated rainfall and analyzed for copper using atomic adsorption. The results of this test demonstrate that less copper is lost from plants treated with the bacterial/fungicide of Example 5 than is lost from plants treated with the wettable powder formulations of copper hydroxide. Greater rainfastness also provides better biological activity since the bactericide/fungicide remains on the treated plant to a greater extent.

| Copper Fungicide | % Cu | 0 | Rainfall (Inches) 0.5 $\mu$g Cu/cm$^2$ leaf area | 2.0 | % Lost After 0.5" | After 2.0" |
|---|---|---|---|---|---|---|
| Example 5 | 40 | 13.0 | 9.9 | 7.4 | 24 | 43 |
| Kocide 101 | 50 | 13.6 | 7.5 | 6.5 | 45 | 52 |
| Blue Shield | 50 | 15.5 | 5.7 | 5.1 | 63 | 67 |

The foregoing description relates to certain embodiments of the present invention, and modifications or alterations may be made therein without departing from the spirit and scope of the invention as defined in the following claims.

We claim:

1. A method of producing a dry flowable bactericide/fungicide for agricultural uses which is substantially nonphytotoxic and which has improved biological activity and rainfastness comprising the steps of:
    forming an aqueous slurry by combining with water:
    between approximately 5% and 20% by weight (based on the total weight of all dry ingredients) of a first dispersant consisting of partially neutralized polyacrylic acid having a pH of between approximately 5 and 10 and an average molecular weight of between approximately 1,000 and 10,000 and also containing between 0 and 20 percent of lignin sulfonate;
    between approximately 0% and 5% by weight (based on the total weight of all dry ingredients) of a second dispersant for bentonite clay;
    between approximately 40% and 80% by weight (based on the total weight of all dry ingredients) phosphate stabilized cupric hydroxide; and
    between approximately 6% and 30% by weight (based on the total weight of all dry ingredients) bentonite clay;
    mixing said slurry to form a substantially homogeneous slurry; and
    drying said slurry to thereby form a free flowing granular material having less than 10% moisture, said granular material being dispersible in aqueous medium.

2. The method of claim 1 further comprising the step of adding between approximately 0.03% and 1% by weight (based on the total weight of all dry ingredients) of an antifoam compound and between 0.03% and 1% by weight (based on the total weight of all dry ingredients) of a wetting agent.

3. The method of claim 1 further comprising the step of milling the homogeneous slurry such that the particles of said slurry have an average particle size of between approximately 0.5 and 3.0 microns.

4. The method of claim 1, wherein said slurry is dried using a spray dryer having an inlet temperature between approximately 350° and 480° F. and an outlet temperature between approximately 150° and 260° F.

5. The method of claim 1, wherein said first dispersant is sodium polyacrylate.

6. The method of claim 4, wherein said first dispersant is sodium polyacrylate.

7. The method of claim 1, wherein said first dispersant is sodium lignin sulfonate.

8. The method of claim 4, wherein said first dispersant is sodium lignin sulfonate.

9. The method of claim 2, wherein said antifoam agent is selected from the group consisting of a surfactant having the formula $C_{14}H_{26}O_2$ dissolved in ethylene glycol and a dimethylsilicone emulsion and said wetting agent is an anionic, polymer-type dispersant.

10. The method of claim 1, wherein said second dispersant is selected from the group consisting of sodium tripolyphosphate, tetrasodium pyrophosphate and sodium lignin sulfonate.

11. A method of producing a dry flowable bactericide/fungicide for agricultural uses which is substantially nonphytotoxic and which has improved biological activity and rainfastness comprising the steps of:

forming an aqueous slurry by combining with water:
between approximately 5% and 20% by weight (based on the total weight of all dry ingredients) of a first dispersant comprising a partially neutralized polycarboxylic acid having a pH of between approximately 5 and 10 and an average molecular weight of between approximately 1,000 and 10,000 said polycarboxylic acid being selected from the group consisting of polymethacrylic acid, copolymers of acrylic acid and acrylamide, copolymers of acrylic acid and methacrylamide, copolymers of acrylic acid and acrylate esters, copolymers of acrylic acid and methacrylic acid, copolymers of acrylic acid and methacrylate esters, copolymers of acrylic acid and maleic anhydride, copolymers of maleic acid and butadiene and polymers of maleic acid and maleic anhydride;
between approximately 0% and 5% by weight (based on the total weight of all dry ingredients) of a second dispersant for bentonite clay;
between approximately 40% and 80% by weight (based on the total weight of all dry ingredients) phosphate stabilized cupric hydroxide; and
between approximately 6% and 30% by weight (based on the total weight of all dry ingredients) bentonite clay;
mixing said slurry to form a substantially homogeneous slurry; and
drying said slurry to thereby form a free flowing granular material having less than 10% moisture, said granular material being dispersible in aqueous medium.

12. A dry flowable formulation of cupric hydroxide made in accordance with the method of claim 1.

13. A dry flowable formulation of cupric hydroxide made in accordance with the method of claim 2.

14. A dry flowable formulation of cupric hydroxide made in accordance with the method of claim 3.

15. A dry flowable formulation of cupric hydroxide made in accordance with the method of claim 4.

16. A dry flowable formulation of cupric hydroxide made in accordance with the method of claim 5.

17. A dry flowable formulation of cupric hydroxide made in accordance with the method of claim 6.

18. A dry flowable formulation of cupric hydroxide made in accordance with the method of claim 7.

19. A dry flowable formulation of cupric hydroxide made in accordance with the method of claim 8.

20. A dry flowable formulation of cupric hydroxide made in accordance with the method of claim 9.

21. A dry flowable formulation of cupric hydroxide made in accordance with the method of claim 10.

22. A dry flowable formulation of cupric hydroxide made in accordance with the method of claim 11.

23. A dry flowable granular formulation of cupric hydroxide for agricultural uses which is substantially nonphytotoxic and which has improved biological activity and rainfastness consisting essentially of:
between approximately 40% and 80% by weight (based on the total weight of all dry ingredients) phosphate stabilized cupric hydroxide;
between approximately 5% and 20% by weight (based on the total weight of all dry ingredients) of a first dispersant consisting of partially neutralized polyacrylic acid having a pH of between approximately 5 and 10 and an average molecular weight of between approximately 1,000 and 10,000 and also containing between 0 and 20 percent of lignin sulfonate;
between approximately 0% and 5% by weight (based on the total weight of all dry ingredients) of a dispersant for bentonite clay;
between approximately 6% and 30% by weight (based on the total weight of all dry ingredients) bentonite clay; and
less than 10% by weight water, said granular formulation being dispersible in aqueous medium.

24. The dry flowable granular formulation of claim 23 further consisting essentially of between approximately 0.03% and 1% by weight (based on the total weight of all dry ingredients) of an antifoam agent is selected from the group consisting of a surfactant having the formula $C_{14}H_{26}O_2$ dissolved in ethylene glycol and a dimethylsilicone emulsion and between approximately 0.03% and 1% by weight (based on the total weight of all dry ingredients) of an anionic, polymer-type dispersant.

25. A method of controlling bacterial/fungal diseases in plants comprising the step of applying to said plants a bactericide/fungicide made in accordance with the method of claim 1.

26. The method of claim 25, wherein said bactericide/fungicide is applied to said leaves by mixing said bactericide/fungicide with water and spraying said bactericide/fungicide onto said leaves.

27. A method of controlling bacterial/fungal diseases in plants comprising the step of applying to said plants an aqueous dispersion of a dry bactericide/fungicide composition which is substantially nonphytotoxic and which has improved biological activity and rainfastness consisting essentially of:
between approximately 40% and 80% by weight (based on the total weight of all dry ingredients) phosphate stabilized cupric hydroxide;
between approximately 5% and 20% by weight (based on the total weight of all dry ingredients) of a first dispersant consisting of partially neutralized polyacrylic acid having a pH of between approximately 5 and 10 and an average molecular weight of between approximately 1,000 and 10,000 and also containing between 0 and 20 percent of lignin sulfonate;
between approximately 0% and 5% by weight (based on the total weight of all dry ingredients) of a dispersant for bentonite clay; and
between approximately 6% and 30% by weight (based on the total weight of all dry ingredients) bentonite clay.

28. The method of claim 27 wherein said bactericide/fungicide composition further consists essentially of between approximately 0.03% and 1% by weight (based on the total weight of all dry ingredients) of an antifoam compound and between 0.03% and 1% by weight (based on the total weight of all dry ingredients) of a wetting agent.

29. The method of claim 28, wherein said antifoam agent is selected from the group consisting of a surfactant having the formula $C_{14}H_{26}O_2$ dissolved in ethylene glycol and a dimethylsilicone emulsion and said wetting agent is an anionic, polymer-type dispersant.

30. A method of controlling bacterial/fungal diseases in plants comprising the step of applying to said plants an aqueous dispersion of a dry bactericide/fungicide composition which is substantially nonphytotoxic and which has improved biological activity and rainfastness consisting essentially of:
- between approximately 40% and 80% by weight (based on the total weight of all dry ingredients) phosphate stabilized cupric hydroxide;
- between approximately 5% and 20% by weight (based on the total weight of all dry ingredients) of a first dispersant comprising a partially neutralized polycarboxylic acid having a pH of between approximately 5 and 10 and an average molecular weight of between approximately 1,000 and 10,000 said polycarboxylic acid being selected from the group consisting of polymethacrylic acid, copolymers of acrylic acid and acrylamide, copolymers of acrylic acid and methacrylamide, copolymers of acrylic acid and acrylate esters, copolymers of acrylic acid and methacrylic acid, copolymers of acrylic acid and methacrylate esters, copolymers of acrylic acid and maleic anhydride, copolymers of maleic acid and butadiene and polymers of maleic acid and maleic anhydride;
- between approximately 0% and 5% by weight (based on the total weight of all dry ingredients) of a dispersant for bentonite clay; and
- between approximately 6% and 30% by weight (based on the total weight of all dry ingredients) bentonite clay.

* * * * *